United States Patent
Ko et al.

(10) Patent No.: US 9,125,963 B2
(45) Date of Patent: Sep. 8, 2015

(54) WOUND DRESSING

(71) Applicant: BIO-MEDICAL CARBON TECHNOLOGY CO., LTD., Taichung (TW)

(72) Inventors: Tse-Hao Ko, Taichung (TW); Ching-Han Liu, Taichung (TW); Jui-Hsiang Lin, Taichung (TW); Yen-Ju Su, Taichung (TW)

(73) Assignee: BIO-MEDICAL CARBON TECHNOLOGY CO., LTD., Taichung (TW)

(*) Notice: Subject to any disclaimer, the term of this patent is extended or adjusted under 35 U.S.C. 154(b) by 106 days.

(21) Appl. No.: 13/953,275

(22) Filed: Jul. 29, 2013

(65) Prior Publication Data
US 2015/0032069 A1    Jan. 29, 2015

(51) Int. Cl.
| | | |
|---|---|---|
| *A61M 27/00* | (2006.01) | |
| *A61F 13/15* | (2006.01) | |
| *A61F 13/00* | (2006.01) | |
| *A61F 13/02* | (2006.01) | |
| *A61L 15/26* | (2006.01) | |
| *A61L 15/58* | (2006.01) | |

(52) U.S. Cl.
CPC .......... *A61L 15/26* (2013.01); *A61F 13/00017* (2013.01); *A61F 13/00029* (2013.01); *A61L 15/58* (2013.01)

(58) Field of Classification Search
CPC .............. A61F 13/8405; A61F 2013/00089; A61F 2013/00314
USPC .................... 604/543, 304, 307, 367
See application file for complete search history.

(56) References Cited

U.S. PATENT DOCUMENTS

| | | | |
|---|---|---|---|
| 2002/0110689 A1* | 8/2002 | Hu et al. .......... | 428/375 |
| 2004/0121688 A1* | 6/2004 | Edens et al. ........ | 442/328 |
| 2004/0166248 A1* | 8/2004 | Hu et al. .......... | 427/553 |

* cited by examiner

*Primary Examiner* — Jacqueline Stephens
(74) *Attorney, Agent, or Firm* — Muncy, Geissler, Olds & Lowe, P.C.

(57) ABSTRACT

A wound dressing for covering a wound includes a textile layer woven by polyacrylonitrile-based activated carbon fiber, and an absorbent layer provided on one side of the textile layer away from the wound. The activated carbon fiber is produced by polyacrylonitrile oxidized fiber in a moisturized carbon dioxide atmosphere at the temperature of 700° C. to 1200° C. for 1 to 60 minutes. The material of the absorbent layer is cotton, alginate, poly vinyl alcohol, or a combination thereof. The water absorbing ability of the absorbent layer is superior to that of the textile layer. Because the textile layer does not produce dust and can keep dry, the hard-to-heal wounds can be prevented.

9 Claims, 2 Drawing Sheets

WOUND DRESSING

BACKGROUND OF THE INVENTION

1. Field of the Invention

The present invention relates generally to a wound dressing and more particularly, to a wound dressing formed of a textile layer and an absorbent layer.

2. Description of the Related Art

In the medical field, the activated carbon material is often applied to manufacture of wound covering because the absorption ability of the activated carbon material is superior to that of the conventional medical gauze. However, it cannot be averted that the activated carbon dust may be produced from the activated carbon textile made of pitch or cellulose by the existing craftsmanship. If the activated carbon dust falls into the wound carelessly, the healing of the wound will become difficult.

In addition, the wound dressing made of the activated carbon material having excellent absorption ability may absorb excessive exudation from a wound when the wound produces greater amount of exudation or the wound dressing is not replaced in time, so the wound may be too wet to heal better.

SUMMARY OF THE INVENTION

The main objective of the present invention is to provide a wound dressing that can keep the wound dry and has activated carbon textile which can directly contact the wound and not generate any dust.

In order to achieve the aforesaid objective, the wound dressing for covering a wound of the present invention includes a textile layer and an absorbent layer. The textile layer is woven by polyacrylonitrile-based activated carbon fiber that is produced by polyacrylonitrile oxidized fiber in a moisturized carbon dioxide atmosphere at a temperature of 700° C. to 1200° C. for 1 to 60 minutes. The absorbent layer is provided on one side of the textile layer away from the wound and the material of the absorbent layer may be cotton, alginate, poly vinyl alcohol, or a combination thereof. Besides, the water absorbing ability of the absorbent layer is superior to that of the textile layer.

Because the textile layer of the wound dressing does not produce dust, it can be in direct contact with the wound to help the wound to heal. In addition, the water absorbing ability of the absorbent layer is superior to that of the textile layer, so most exudation generating from the wound may be absorbed into the absorbent layer through the textile layer so as to keep the textile layer dry. In this way, it can be avoided that the would is too wet to heal easily.

BRIEF DESCRIPTION OF THE DRAWINGS

The present invention will become more fully understood from the detailed description given herein below and the accompanying drawings which are given by way of illustration only, and are not limitative of the present invention, and wherein.

DETAILED DESCRIPTION OF THE INVENTION

Figure 1:
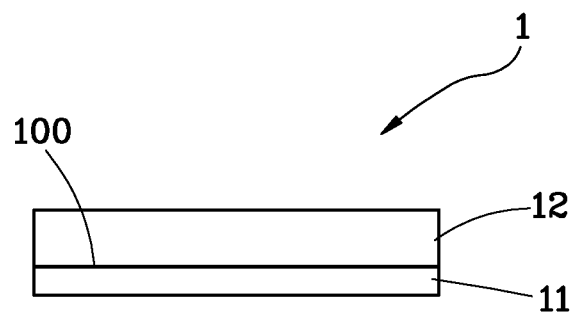
FIG. 1 is a lateral side view of a wound dressing according to a first preferred embodiment of the present invention.

It will be appreciated that in the preferred embodiments to be detailed described hereunder, the same reference numeral represents the same or similar part.

As shown in FIG. 1, the wound dressing 1 provided by a first preferred embodiment of the present invention is used to cover a wound (not shown). The wound dressing 1 comprises a textile layer 11 and an absorbent layer 12.

The textile layer 11 is designed to be in direct contact with the wound and is woven by polyacrylonitrile-based activated carbon fiber. The polyacrylonitrile-based activated carbon fiber is manufactured by the steps of providing a polyacrylonitrile oxidized fiber textile; serving a moisturized carbon dioxide gas, which is manufactured by pass carbon dioxide through water, as an activated gas; placing the polyacrylonitrile oxidized fiber textile in a high-temperature furnace and heating it up to 700° C. to 1200° C. and introducing the activated gas; and keeping them reacted for one minute to one hour so as to obtain the polyacrylonitrile-based activated carbon fiber textile. The polyacrylonitrile-based activated carbon fiber textile thus obtained is properly cut to form the textile layer 11. The inlet and the outlet of the furnace are protected by inert gas to prevent volatile substance of the polyacrylonitrile oxidized fiber textile from spontaneous combustion. Furthermore, the heating temperature is preferably 900° C. to 1000° C.

It is to be noted that the polyacrylonitrile-based activated carbon fiber textile does not produce dust and therefore can be in direct contact with the wound and does not affect wound healing adversely.

The absorbent layer 12 is provided on one side of the textile layer 11 away from the wound and the material of the absorbent layer 12 may be superabsorbent polymer, cotton, alginate, PU foam, poly vinyl alcohol, or a combination thereof. Besides, the water absorbing ability of the absorbent layer 12 is superior to that of the textile layer 11.

In this embodiment of the present invention, a pressure-sensitive adhesive 100 is coated on surfaces of the textile layer 11 and absorbent layer 12. Then, the textile layer 11 and the absorbent layer 12 are pressed to be joined to each other, thereby strengthening the adhesion between the textile layer 11 and the absorbent layer 12. The pressure-sensitive adhesive 100 may be, for example, polyacrylate, siloxane, polyisobutylene, or any suitable pressure-sensitive adhesive. Besides, the textile layer 11 and the absorbent layer 12 can be connected to each other by an appropriate means such as a specific weave method, so the pressure-sensitive adhesive 100 is not necessary in the present invention.

The characteristics of the textile layer 11 are described as follows: First, the activated carbon fiber of the textile layer 11 has a BET specific surface area which is greater than 300 m$^2$/g and preferably ranges from 600 m$^2$/g to 2000 m$^2$/g. Second, based on the total pore volume, the micropore volume of the micropores having a diameter less than 2 nm of the activated carbon fiber of the textile layer 11 is 30% to 70% and preferably 45% to 60%. The pore having a diameter less than 2 nm is defined as a micropore in the present invention. Third, the far-infrared radiation rate is greater than 75%. Fourth, the deodorant rate is greater than 65%. Fifth, the antibacterial rate against *Staphylococcus aureus* is greater than 70%, and preferably greater than 90%. According to AATCC100 standard, the antibacterial rate (%) was calculated using the following formula: C(%)=100×(A−B)/A, where C stands for antibacterial rate, A stands for bacteria counts in a control group, and B stands for bacterial count in a experimental group. The greater the antibacterial rate is, the better the antibacterial effect is. Sixth, the antibacterial rate against *Pseudomonas aeruginosa* is greater than 70% and preferably greater than 90%. The activated carbon fiber textile having a BET specific surface area less than 280 m²/g and the ratio of the micropore volume to the total pore volume less than 30% has significantly poor antibacterial effect, far-infrared radiation rate, and deodorant rate. In addition, the activated carbon fiber textile having a specific surface area greater than 2000 m²/g and the ratio of the micropore volume to the total pore volume greater than 70% is difficult to be manufactured by existing technology.

Please refer to the following test results to fully and clearly understand the effect of the textile layer 11.

Sample 1: The textile layer 11 is the polyacrylonitrile-based activated carbon fiber textile (not shown) manufactured by the process described above on condition that the temperature is 1000 and the reaction time is 5 minutes. The polyacrylonitrile-based activated carbon fiber textile has a weight of 90 g/m², a specific surface area of 1000 m²/g, and a micropore volume of 52% based on total pore volume. A cotton (not shown) serving as the absorbent layer 12 is adhered to the polyacrylonitrile-based activated carbon fiber textile through a polyacrylate pressure-sensitive adhesive to form a laminar wound dressing 1 as shown in FIG. 1.

The test results of sample 1 are recited below and summarized in Table 1 shown below. The antibacterial rate against *Staphylococcus aureus* and *Pseudomonas aeruginosa* is 99.9% according to AATTCC 100 standard, the far-infrared radiation rate is 89% according to JSC-3 standard, and the deodorant rate of ammonia is 87% evaluated from Japan's JAFET test. Besides, after the sample 1 is applied to the wrist of human hand for one hour, the temperature of the area covered by sample 1 increases for 2° C.

Samples 2 and 3: The textile layer 11 of the sample 2 is the polyacrylonitrile-based activated carbon fiber textile manufactured by the process described above on condition that the temperature is 700° C. and the reaction time is 5 minutes, and the textile layer 11 of sample 3 is the polyacrylonitrile-based activated carbon fiber textile manufactured by the process described above on condition that the temperature is 900° C. and the reaction time is 5 minutes. Sample 2 has a specific surface area of 300 m²/g, and a micropore volume of 34% based on total pore volume. Sample 3 has a specific surface area of 400 m²/g, and a micropore volume of 38% based on total pore volume. The adhesion method applied to the textile layer 11 and the absorbent layer 12 is the same as that of the sample 1. Besides, the samples 2 and 3 are evaluated by the same criteria and the results are listed in Table 1 shown below.

Samples 4 and 5: The textile layer 11 of the sample 4 is the polyacrylonitrile-based activated carbon fiber textile manufactured by the process described above on condition that the temperature is 1000° C. and the reaction time is 30 minutes, and the textile layer 11 of the sample 5 is the polyacrylonitrile-based activated carbon fiber textile manufactured by the process described above on condition that the temperature is 1000° C. and the reaction time is 60 minutes. The sample 4 has a specific surface area of 1500 m²/g, and a micropore volume of 51% based on total pore volume. The sample 5 has a specific surface area of 2000 m²/g, and a micropore volume of 49% based on total pore volume. The adhesion method applied to the textile layer 11 and the absorbent layer 12 is the same as that of the sample 1. Besides, the samples 4 and 5 are evaluated by the same criteria and the results are listed in Table 1 shown below.

Comparative samples A and B: The textile layer 11 of the comparative sample A is the polyacrylonitrile-based activated carbon fiber textile manufactured by the process described above on condition that the temperature is 500° C. and the reaction time is 5 minutes, and the textile layer 11 of the comparative sample B is the polyacrylonitrile-based activated carbon fiber textile manufactured by the process described above on condition that the temperature is 600° C. and the reaction time is 5 minutes. The comparative sample A has a specific surface area of 100 m²/g, and a micropore volume of 10% based on total pore volume. The comparative sample B has a specific surface area of 280 m²/g, and a micropore volume of 27% based on total pore volume. The adhesion method applied to the textile layer 11 and the absorbent layer 12 is the same as that of the sample 1. Besides, the comparative samples A and B are evaluated by the same criteria and the results are listed in Table 1 shown below

TABLE 1

|  | A1 (° C.) | A2 (m²/g) | A3 (%) | A4 (%) | A5 (%) | A6 (%) | A7 (%) |
| --- | --- | --- | --- | --- | --- | --- | --- |
| Sample 1 | 1000 | 1000 | 52 | 89 | 87 | 99.9 | 99.9 |
| Sample 2 | 700 | 300 | 34 | 81 | 69 | 90.2 | 90.4 |
| Sample 3 | 900 | 400 | 38 | 83 | 74 | 92.4 | 91.9 |
| Sample 4 | 1000 | 1500 | 51 | 88 | 89 | 99.95 | 99.95 |
| Sample 5 | 1000 | 2000 | 49 | 87 | 91 | 99.95 | 99.95 |
| Comparative Sample A | 500 | 100 | 10 | 65 | 58 | 39.6 | 40.1 |
| Comparative Sample B | 600 | 280 | 27 | 66 | 62 | 42.1 | 41.8 |

In Table 1, A1 to A7 stand for Activated Temperature, BET Specific Surface Area, Micropore Volume based on Total Pore Volume, Far-Infrared Radiation Rate, Deodorant Rate, Antibacterial Rate against *Staphylococcus aureus*, and Antibacterial Rate against *Pseudomonas aeruginosa*, respectively.

As can be seen from the test results of Table 1: First, the samples 1 to 5 in which the BET specific surface area is in a range of 300 m²/g to 2000 m²/g and the micropore volume based on total pore volume is between 30% and 70% have better far-infrared radiation rate, deodorant rate, and antibacterial rate against *Staphylococcus aureus* and *Pseudomonas aeruginosa*. Second, the comparative samples A and B in which the BET specific surface area is less than 280 m²/g and the micropore volume based on based on total pore volume is less than 30% have poor far-infrared radiation rate, deodorant rate, and antibacterial rate against *Staphylococcus aureus* and *Pseudomonas aeruginosa*.

The wound dressing 1 having the textile layer 11 and the absorbent layer 12 attached to each other of the present invention has the following advantages: 1. the textile layer 11 woven by polyacrylonitrile (PAN)-based activated carbon fiber does not produce dust and thus can be in direct contact with the wound and does not adversely affect wound healing; 2. the textile layer 11 can help the wound healing since the textile layer 11 includes polyacrylonitrile-based activated carbon fiber having excellent deodorant effect and antibacterial effect and is capable of emitting far-infrared radiation which can improve blood circulation; 3. the hard-to-heal wound can be prevented since the absorbent layer 12 has superior water absorbing ability than those of the textile layer 11 and conventional absorbent layer such that most of the exudation is absorbed into the absorbent layer 12 to keep the textile layer 11 dry.

Figure 2:
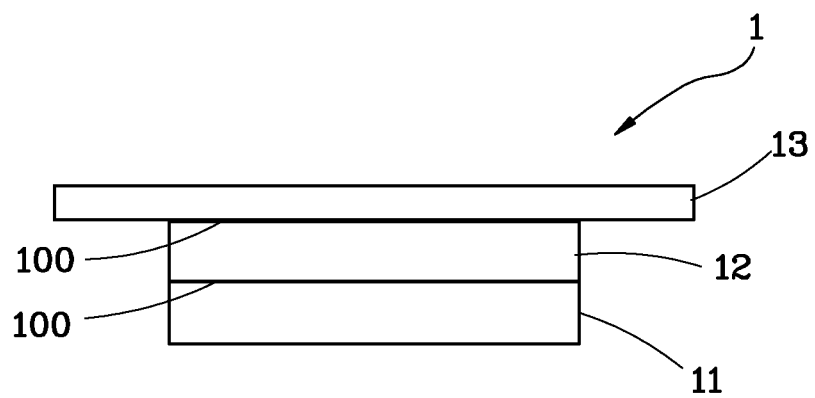
FIG. 2 is a lateral side view of a wound dressing according to a second preferred embodiment of the present invention.

As shown in FIG. 2, a wound dressing 1 according to a second preferred embodiment of the present invention is structurally similar to that of the wound dressing 1 of the first preferred embodiment. The difference between the first and the second preferred embodiments lies in that that the wound dressing 1 further comprises a protection layer 13 provided on one side of the absorbent layer 12 away from the wound so as to cover and protect the textile layer 11 and the absorbent layer 12. Every material serving as the protection layer of the conventional wound dressing can be applied to the present invention, such as polyethylene, polyurethane, Nylon, polyamide, polycellulose, polyvinyl chloride, polyvinyl dichloride, polyolefin, polyurea, polyester, etc. However, the protection layer 13 can be omitted according to actual needs.

Figure 3:
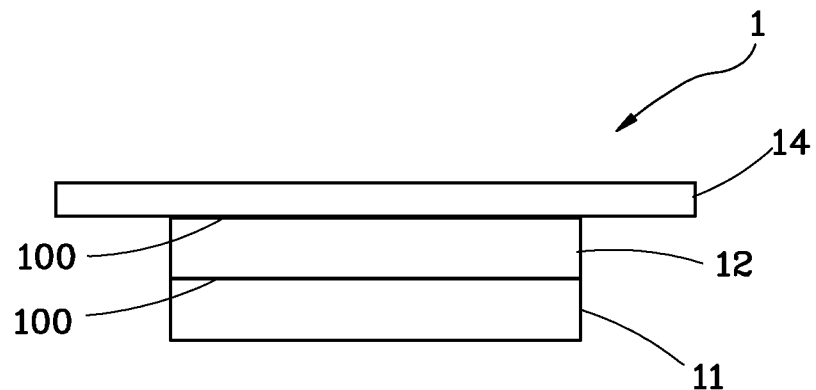
FIG. 3 is a lateral side view of a wound dressing according to a third preferred embodiment of the present invention.

As shown in FIG. 3, a wound dressing 1 according to a third preferred embodiment of the present invention is structurally similar to that of the wound dressing 1 of the first preferred embodiment. The difference between the first and the third preferred embodiments lies in that the wound dressing 1 further comprises a water-resist breathable layer 14 provided on one side of the absorbent layer 12 away from the wound so as to prevent the absorbent layer 12 from leakage of exudation when the absorbent layer 12 is saturated with exudation. Further, the water-resist breathable layer 14 can also prevent any liquid inhibiting wound healing from entering the textile layer 11. Every material serving as the waterproof breathable layer of the conventional wound dressing can be applied to the present invention, such as PU resin, W/O type emulsion resin, polytetrafluoroethylene, etc. However, the waterproof breathable layer 14 can be omitted according to actual needs.

Figure 4:
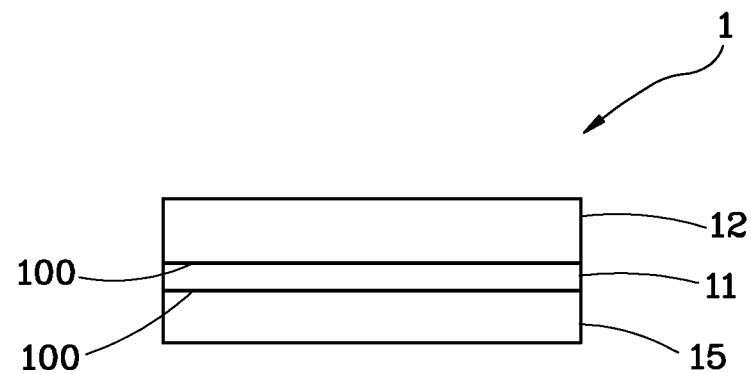
FIG. 4 is a lateral side view of a wound dressing according to a fourth preferred embodiment of the present invention.

As shown in FIG. 4, a wound dressing 1 according to a fourth preferred embodiment of the present invention is structurally similar to that of the wound dressing 1 of the first preferred embodiment. The difference between the first and the fourth preferred embodiments lies in that the wound dressing 1 further comprises an anti-adhesion layer 15 provided on one side of the textile layer 11 adjacent to the wound for contact with the wound. Besides, the anti-adhesion layer 15 is made of porous material and every material serving as anti-adhesion layer of the conventional wound dressing can be applied to the present invention, such as natural fiber, polyethylene fiber, polyolefin fiber, polyester fiber, polyurethane fiber, polyamide fiber, polycellulose fiber, cotton fiber, etc. Films, woven fabrics, or non-woven fabrics made of the aforesaid materials are porous to allow blood or body fluid to flow therethrough. Further, the anti-adhesion layer 15 is not easily adhered to the wound, so the anti-adhesion layer 15 will not hurt the wound when the wound dressing 1 is replaced. However, the anti-adhesion layer 15 can be omitted according to actual needs.

Structural variations of the wound dressing can be made in the present invention. For example, the wound dressing can have both of the protection layer 13 and the anti-adhesion layer 15 and thus the textile layer 11 and the absorbent layer 12 are sandwiched between the protection layer 13 and the anti-adhesion layer 15. For example, the wound dressing can have both of the waterproof breathable layer 14 and the anti-adhesion layer 15. Accordingly, every equivalent modification or variation is also included within the scope of the present invention.

What is claimed is:

1. A wound dressing for covering a wound, comprising:
   a textile layer woven by polyacrylonitrile-based activated carbon fiber that is produced by polyacrylonitrile oxidized fiber in a moisturized carbon dioxide atmosphere at the temperature of 700° C. to 1200° C. for 1 to 60 minutes; and
   an absorbent layer disposed on one side of said textile layer away from the wound and made of superior water absorbing polymer, cotton, alginate, poly vinyl alcohol, polyurethane foam or a combination thereof, said absorbent layer having a superior water absorbing ability to that of said textile layer,
   wherein the activated carbon fiber of said textile layer has a ratio of a micropore volume of micropores having a diameter less than 2 nm to a total pore volume ranging from 30% to 70%.

2. The wound dressing as claimed in claim 1, wherein the ratio of the micropore volume of micropores having a diameter less than 2 nm to the total pore volume ranges from 45% to 60%.

3. The wound dressing as claimed in claim 1, wherein the activated carbon fiber of said textile layer comprises a BET specific surface area ranging from 300 $m^2/g$ to 2000 $m^2/g$.

4. The wound dressing as claimed in claim 1, wherein said textile layer comprises a far-infrared radiation rate greater than 75%.

5. The wound dressing as claimed in claim 1, wherein said textile layer comprises a deodorant rate greater than 65%.

6. The wound dressing as claimed in claim 1, wherein said textile layer comprises an antibacterial rate against *Staphylococcus aureus* and *Pseudomonas aeruginosa* which is greater than 70%.

7. The wound dressing as claimed in claim 1, further comprising a protection layer disposed on one side of said absorbent layer away from the wound.

8. The wound dressing as claimed in claim 1, further comprising a water-resist breathable layer disposed on one side of said absorbent layer away from the wound.

9. The wound dressing as claimed in claim 1, further comprising an anti-adhesion layer disposed on one side of said textile layer opposite to the absorbent layer for contact with the wound.

* * * * *